(12) United States Patent
Atsumi et al.

(10) Patent No.: US 9,737,706 B2
(45) Date of Patent: Aug. 22, 2017

(54) ELECTROSTIMULATOR AND CONTROL DEVICE OF SAME

(71) Applicant: Panasonic Intellectual Property Management Co., Ltd., Osaka (JP)

(72) Inventors: Sachiko Atsumi, Shiga (JP); Tadashi Arimura, Kyoto (JP); Hiroyuki Kaizo, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/133,340

(22) Filed: Apr. 20, 2016

(65) Prior Publication Data

US 2016/0346538 A1    Dec. 1, 2016

(30) Foreign Application Priority Data

May 27, 2015 (JP) ................. 2015-107956

(51) Int. Cl.
*A61N 1/36* (2006.01)
*A61N 1/04* (2006.01)
*A61B 5/11* (2006.01)

(52) U.S. Cl.
CPC ............ *A61N 1/36003* (2013.01); *A61B 5/11* (2013.01); *A61N 1/0452* (2013.01); *A61N 1/36014* (2013.01); *A61B 2505/09* (2013.01)

(58) Field of Classification Search
CPC ..................... A61N 1/36003; A61N 1/0452
USPC ..................................... 607/48, 49
See application file for complete search history.

(56) References Cited

U.S. PATENT DOCUMENTS

| 6,456,885 B1 | 9/2002 | Shiba et al. |
| 2013/0211474 A1* | 8/2013 | Nielsen .............. A61N 1/36003 607/49 |

FOREIGN PATENT DOCUMENTS

JP    2000-279536    10/2000

* cited by examiner

*Primary Examiner* — Allen Porter, Jr.
(74) *Attorney, Agent, or Firm* — McDermott Will & Emery LLP (57) ABSTRACT

A control device of an electrostimulator is used in the electrostimulator including an electrode and an angular velocity sensor. The control device includes a controller that controls electrostimulation which is output from the electrode and a storage that stores a first threshold value and a second threshold value. The first threshold value is greater than the second threshold value. The controller causes the electrode to output electrostimulation based on a state in which angular velocity reaches one threshold value of the first threshold value and the second threshold value, and then, reaches the other threshold value.

10 Claims, 5 Drawing Sheets

ELECTROSTIMULATOR AND CONTROL DEVICE OF SAME

BACKGROUND OF THE INVENTION

1. Field of the Invention

The present disclosure relates to an electrostimulator and a control device of the electrostimulator.

2. Description of the Related Art

There has been known an electrostimulator that outputs electrostimulation to an agonist muscle or an antagonist muscle. For example, an electrostimulator disclosed in Japanese Patent Unexamined Publication No. 2000-279536 includes an electrode that outputs electrostimulation to a target site of a human body, a detector that outputs a signal in which motion of the target site is reflected, and a controller that controls the electrostimulation which is output from the electrode in response to the signal from the detector.

According to an example of a configuration of the electrostimulator, a user's leg is equipped with a first electrode and a second electrode so as to be applied with the electrostimulation. In a case where a knee joint is bent due to bending and extension movements, the controller controls the first electrode in response to the signal from the detector such that the electrostimulation is applied to the quadriceps femoris as the antagonist muscle. In addition, in a case where the knee joint is extended due to the bending and extension movements, the controller controls the second electrode in response to the signal from the detector such that the electrostimulation is applied to the biceps femoris as the antagonistic muscle.

SUMMARY OF THE INVENTION

Movement of a user may not be stable during training For example, in a case where the user makes bending and extension movements, there is a difference between motions of the body in ideal bending and extension movements and actual motions of the body due to swaying of the upper body.

In a case where the motion of the user is not stable, signals from the detector may change in response to the motion of the user in a short cycle. According to the electrostimulator in the related art described above, even in such a case, the electrostimulation is output from the electrode in response to the signal from the detector. Therefore, outputting and stopping of the electrostimulation are repeated in a short cycle, and thus, there is a concern that a user will be uncomfortable. Here, a problem arising in a case of using an electrostimulator in bending and extension movements, as an example, is studied; however, it is considered that the same problem also arises in a case of using the electrostimulator during training other than the bending and extension movements.

An object of the present disclosure is to provide an electrostimulator and a control device of the electrostimulator which are unlikely to make a user uncomfortable.

A control device of an electrostimulator according to one aspect of the present disclosure is used in the electrostimulator including an electrode that outputs electrostimulation to a target site of a human body which repeats reciprocating movements, and a detector that outputs a signal in which the motion of the target site is reflected. The control device includes: a controller that controls electrostimulation which is output from the electrode based on a detected value obtained in response to the signal from the detector; and a storage that stores a first threshold value which is compared with the detected value so as to control an outputting state from the electrode, and a second threshold value which is compared with the detected value so as to control the outputting state from the electrode and which is smaller than the first threshold value. The controller causes the electrode to output electrostimulation based on a state in which the detected value reaches one threshold value of the first threshold value and the second threshold value, and then, reaches the other threshold value.

An electrostimulator according to another aspect of the present disclosure includes an electrode, a detector, and the control device.

The electrostimulator and the control device of the electrostimulator are unlikely to make a user uncomfortable.

DETAILED DESCRIPTION OF THE PREFERRED EMBODIMENTS

Example of Exemplary Embodiment of Electrostimulator and Control Device of Same A control device of an electrostimulator according to a first aspect of the present disclosure is used in the electrostimulator including an electrode that outputs electrostimulation to a target site of a human body which repeats reciprocating movements, and a detector that outputs a signal in which the motion of the target site is reflected. The control device includes: a controller that controls electrostimulation which is output from the electrode based on a detected value obtained in response to the signal from the detector; and a storage that stores a first threshold value which is compared with the detected value so as to control an outputting state from the electrode, and a second threshold value which is compared with the detected value so as to control the outputting state from the electrode and which is smaller than the first threshold value. The controller causes the electrode to output electrostimulation based on a state in which the detected value reaches one threshold value of the first threshold value and the second threshold value, and then, reaches the other threshold value.

According to the control device of the electrostimulator, although the detected value changes due to an unstable motion of a user and, for example, the detected value exceeds the first threshold value, the electrostimulation is not output from the electrode when the detected value does not reach the second threshold value. Therefore, there is less concern that the outputting and the stopping of the electrostimulation will be repeated in a short cycle and the user is unlikely to be uncomfortable.

According to a second aspect of the control device of the electrostimulator, in the case where electrostimulation is output from the electrode, the controller causes the outputting from the electrode to be stopped, based on a state in which the detected value reaches the first threshold value or the second threshold value.

According to the control device of the electrostimulator, the first threshold value or the second threshold value is used not only for outputting the electrostimulation from the electrode, but also for stopping the outputting from the electrode. Therefore, the amount of information required to be stored in the control device in advance is decreased.

According to a third aspect of the control device of the electrostimulator, a sign of the first threshold value is opposite to a sign of the second threshold value.

The reciprocating movement includes a first period during which the target site moves from an initial position to a folded position, and a second period during which the target site moves from the folded position to the initial position. A typical example of an unstable motion of a user is a motion in which a speed of the motion of the target site is changed within the first period or within the second period. Therefore, in the case where the sign of the first threshold value is opposite to the sign of the second threshold value as in the control device of the electrostimulator, there is still less concern that the outputting and the stopping of the electrostimulation will be repeated in a short cycle, even though the detected value changes due to the unstable motion of the user.

According to a fourth aspect of the control device of the electrostimulator, the controller calculates a post-stop time period as a period of elapsed time after the outputting from the electrode is stopped, based on a state in which the detected value reaches one threshold value of the first threshold value and the second threshold value, and then, reaches the other threshold value in a case where output from the electrode is stopped. Then, the controller maintains a state in which the outputting from the electrode is stopped in a case where the calculated post-stop time period is shorter than a predetermined post-stop time period.

Since, in the case of the unstable motion of the user, the target site vibrates in the short cycle, for example, the post-stop time period becomes shorter. Therefore, the outputting state from the electrode is controlled as in the control device of the electrostimulator, thereby being unlikely to repeat the outputting and the stopping of the electrostimulation in a short cycle, even though the detected value changes in the short cycle due to the unstable motion of the user.

According to a fifth aspect of the control device of the electrostimulator, the controller calculates a post-output time period as a period of elapsed time after the latest electrostimulation is output from the electrode, based on a state in which the detected value reaches one threshold value of the first threshold value and the second threshold value, and then, reaches the other threshold value in a case where the outputting from the electrode is stopped. The controller maintains a state in which the outputting from the electrode is stopped in a case where the calculated post-output time period is shorter than a predetermined post-output time period.

Since, in the case of the unstable motion of the user, the target site vibrates in the short cycle, for example, the post-output time period becomes shorter. Therefore, the outputting state from the electrode is controlled as in the control device of the electrostimulator, thereby being unlikely to repeat the outputting and the stopping of the electrostimulation in a short cycle, even though the detected value changes in the short cycle due to the unstable motion of the user.

According to a sixth aspect of the control device of the electrostimulator, the controller causes the outputting from the electrode to be stopped, based on a state in which a period of time for which the detected value is within a predetermined range including the detected value of 0 is equal to or longer than a predetermined period of time.

In a case where the motion of the user is stopped, the state in which the detected value is within the predetermined range including the detected value of 0 is maintained. Therefore, the outputting state from the electrode is controlled as in the control device of the electrostimulator, and thereby electrostimulation is not output from the electrode in the case where the motion of the user is stopped.

An electrostimulator according to another aspect of the present disclosure includes: an electrode; a detector; and the control device according to any one of first aspect to sixth aspect above.

According to the electrostimulator, virtually the same effects as the effects achieved by the control device of the electrostimulator according to first aspect to sixth aspect above are achieved.

Exemplary Embodiment 1

Figure 1:
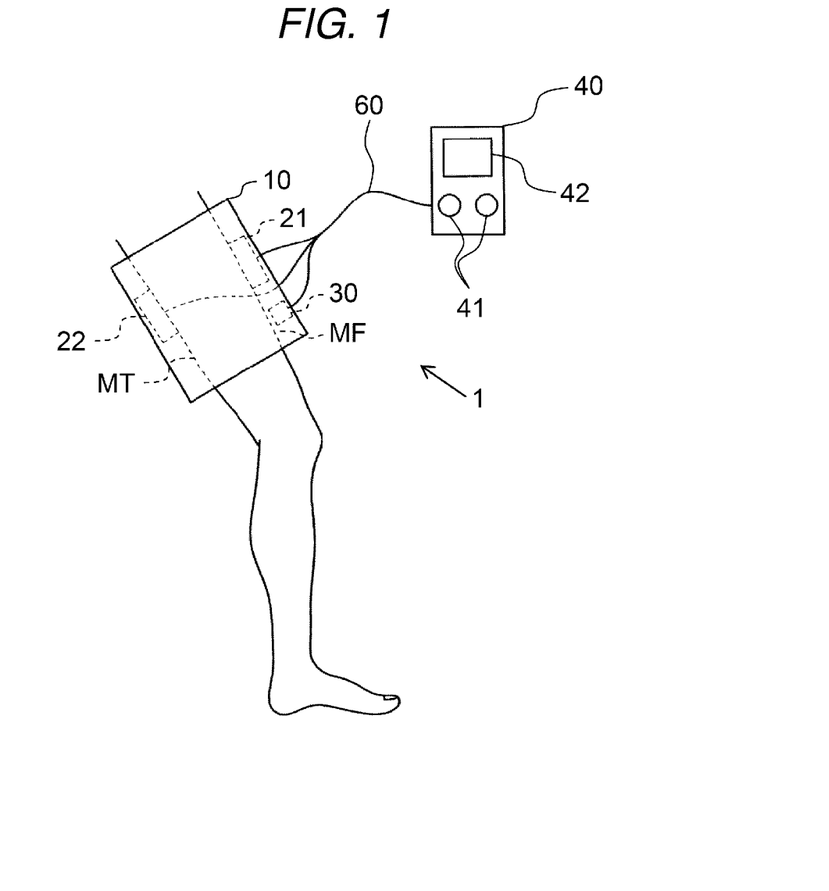
FIG. 1 is a schematic view illustrating an electrostimulator of Exemplary Embodiment 1.

FIG. 1 illustrates an example of a state of use of electrostimulator 1. Electrostimulator 1 includes a pair of supporters 10 put on a target site of a human body, which repeats reciprocating movements, first electrode 21 and second electrode 22 attached on an inner surface of each of supporters 10 so as to be exposed to the outside, and angular velocity sensor 30, as a detector, which is attached to each of supporters 10. In a case where electrostimulator 1 is used during bending and extension movements as an example of the reciprocating movement, supporter 10 is put on a thigh as the target site.

Supporter 10 for a right leg, which is put on a right thigh, and supporter 10 for a left leg, which is put on a left thigh, have a relationship of vertical symmetry with respect to the median plane of a human body. FIG. 1 illustrates supporter 10 for the left leg and supporter 10 for the right leg is omitted.

Each of electrodes 21 and 22 has a positive pole and a negative pole and outputs electrostimulation to muscles of a thigh which repeats bending and extension movements. First electrode 21 is disposed at a position facing quadriceps femoris MF, for example, in the state in which supporter 10 is put on the thigh. Second electrode 22 is disposed at a position facing biceps femoris MT, for example, in the state in which supporter 10 is put on the thigh.

When a knee joint is bent during the bending and extension movements, biceps femoris MT contracts as an agonist muscle and quadriceps femoris MF is extended as an antagonist muscle. On the other hand, when the knee joint is extended during the bending and extension movements, quadriceps femoris MF contracts as the agonist muscle and biceps femoris MT is extended as the antagonist muscle.

Angular velocity sensor 30 outputs a signal, for example, in which an angular velocity of a thigh rotating about a knee joint is reflected. The signal output from angular velocity sensor 30 indicates a positive value when the knee joint is bent and indicates a negative value when the knee joint is extended.

Electrostimulator 1 further includes controller 40 configured of a plurality of electric elements, and cable 60 that electrically connects electrodes 21, 22, angular velocity sensors 30, and controller 40. Controller 40 includes operator 41 for switching between ON and OFF of the power of electrostimulator 1, and notifier 42 on which information is displayed. An example of notifier 42 is a display.

Figure 2:
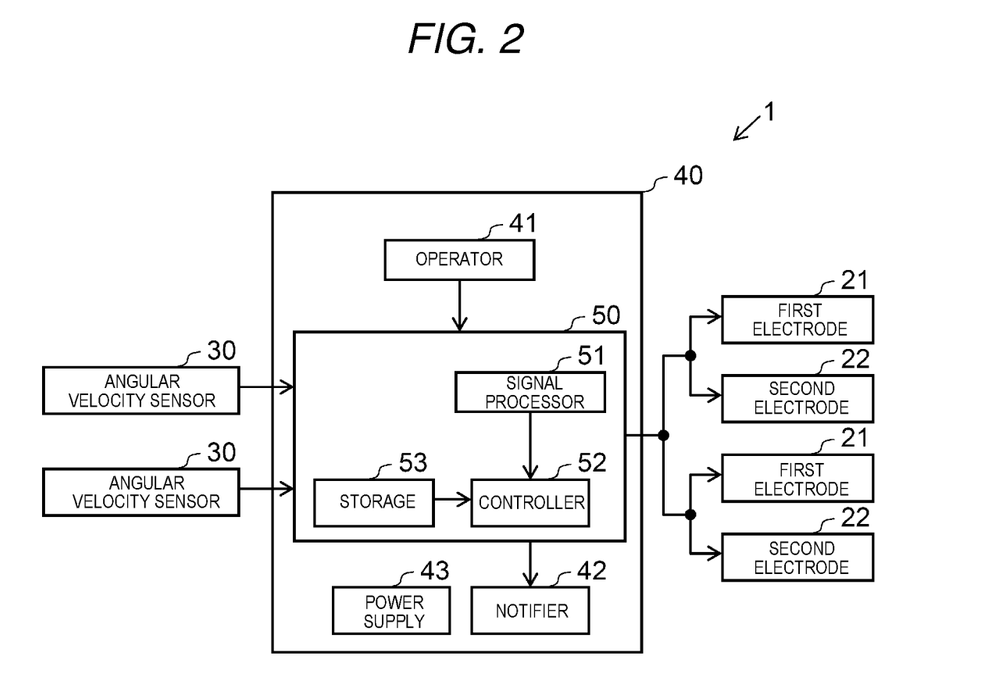
FIG. 2 is a block diagram of the electrostimulator in FIG. 1.

FIG. 2 illustrates a relation of electrical connection of electrostimulator 1. Controller 40 includes control device 50 that acquires a signal from each of angular velocity sensors 30, and power supply 43 that supplies power of a primary battery or a secondary battery to control device 50. Power supply 43 is electrically connected to operator 41 and notifier 42, in addition to control device 50.

Control device 50 includes signal processor 51 that performs a signal process on an input signal, controller 52 that controls electrostimulation which is output from each of electrodes 21 and 22 based on a detected result from each of angular velocity sensors 30, and storage 53 that stores preset information. Controller 52 controls electrodes 21 and 22 attached on supporter 10, for example, based on the detected results from angular velocity sensor 30 attached on one supporter 10 (refer to FIG. 1).

Signal processor 51 performs a signal process on the signal input from angular velocity sensor 30, thereby generating a sine wave signal. The signal processing includes removal of noise of a high frequency component, calculation of an average movement amount, frequency analysis, and the like. Signal processor 51 transmits an angular velocity as a detected value obtained from the generated sine wave signal to controller 52. Controller 52 controls electrostimulation which is output from each of electrodes 21 and 22, based on the angular velocity obtained from signal processor 51.

Storage 53 stores first threshold value T1 which is compared with the angular velocity for controlling an outputting state from each of electrodes 21 and 22, and second threshold value T2 which is compared with the angular velocity for controlling the outputting state from each of electrodes 21 and 22 and which is smaller than first threshold value T1. The sign of first threshold value T1 is opposite to the sign of second threshold value T2. In other words, first threshold value T1 exists in a positive region and second threshold value T2 exists in a negative region.

Controller 52 reads respective threshold values T1 and T2 from storage 53 and causes electrodes 21 and 22 to output electrostimulation, based on a state in which the angular velocity reaches one threshold value of first threshold value T1 or second threshold value T2, and then, reaches the other threshold value. Specifically, controller 52 determines that the angular velocity reaches second threshold value T2, and then, reaches first threshold value T1, thereby causing first electrode 21 to output electrostimulation. Therefore, the electrostimulation is applied to quadriceps femoris MF (refer to FIG. 1) as the antagonist muscle. Then, in a case where the electrostimulation is output from first electrode 21, controller 52 causes the outputting from first electrode 21 to be stopped, based on the state in which the angular velocity reaches second threshold value T2.

In comparison, controller 52 determines that the angular velocity reaches first threshold value T1, and then, reaches second threshold value T2, thereby causing second electrode 22 to output electrostimulation. Therefore, the electrostimulation is applied to biceps femoris MT (refer to FIG. 1) as the antagonist muscle. Then, in a case where the electrostimulation is output from second electrode 22, controller 52 causes the outputting from second electrode 22 to be stopped, based on a state in which the angular velocity reaches first threshold value T1. In this manner, controller 52 performs electrostimulation control that controls the electrostimulation which is output from electrodes 21 and 22, based on a relationship between the angular velocity and each of threshold values T1 and T2. Since the angular velocity is practically set to 0 when the bending and extension movements are started, controller 52 causes electrodes 21 and 22 corresponding to reached threshold values T1 and T2 to output the electrostimulation, based on a state in which the angular velocity reaches one threshold value of first threshold value T1 or second threshold value T2.

Controller 52 includes a timer (not illustrated) that measures a period of time. In a case where the outputting from first electrode 21 is stopped, controller 52 calculates, by using the timer, post-stop time period SA1 as a period of time which elapses after the outputting from first electrode 21 is stopped, based on the state in which the angular velocity reaches first threshold value T1 after reaching second threshold value T2. In addition, in a case where the outputting from second electrode 22 is stopped, controller 52 calculates, by using the timer, post-stop time period SA2 as a period of time which elapses after the outputting from second electrode 22 is stopped, based on the state in which the angular velocity reaches second threshold value T2 after reaching first threshold value T1. In a case where the calculated post-stop time periods SA1 and SA2 are shorter than a predetermined post-stop time period set in advance, controller 52 performs stop-maintaining control of maintaining the state in which the outputting from electrodes 21 and 22 is stopped. The predetermined post-stop time period is stored in storage 53.

Controller 52 calculates, by using the timer, a period of duration time (duration) during which the angular velocity is within a predetermined range including the angular velocity of 0. An example of the predetermined range is a range which is defined by first threshold value T1 and second threshold value T2. Controller 52 performs output-stop control such that the outputting from electrodes 21 and 22 is stopped, based on a state in which the duration reaches determined time period PA as a predetermined period of time set in advance. Determined time period PA is stored in storage 53. Controller 52 performs first control including, for example, the electrostimulation control, the stop-maintaining control, and the output-stop control, and controls the electrostimulation which is output from each of electrodes 21 and 22.

Figure 3A:
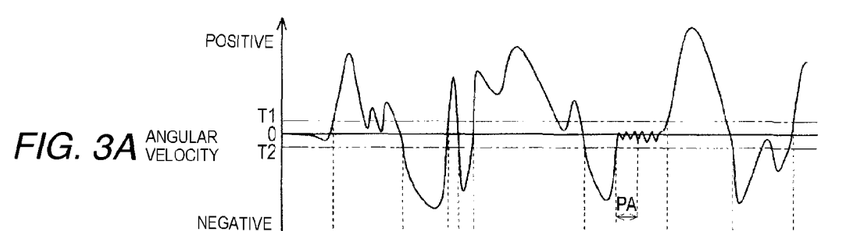
FIGS. 3A to 3C are time charts showing an example of first control.
Figure 3B:
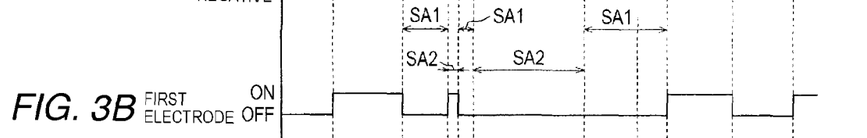
Figure 3C:
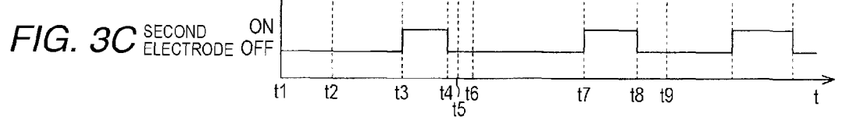

FIGS. 3A to 3C illustrate an example of a relationship between the angular velocity related to training and the outputting states from electrodes 21 and 22 when the first control is performed. A temporal change of the angular velocity is shown in FIG. 3A, the outputting state from first electrode 21 is shown in FIG. 3B, and the outputting state from second electrode 22 is shown in FIG. 3C. In addition, since virtually the same detection results are obtained from respective angular velocity sensors 30 during the bending and extension movements, a relationship between the angular velocity acquired from one angular velocity sensor 30 and electrodes 21 and 22 corresponding to one angular velocity sensor 30 is described.

At time point t1, a user using electrostimulator 1 operates operator 41 so as to switch the power of electrostimulator 1 from OFF to ON. The power of electrostimulator 1 is set to ON, and thereby each of angular velocity sensors 30 starts outputting, to controller 52, a signal, in which an angular velocity of a thigh is reflected. Then, the user starts, for example, training by cyclic bending and extension movements from a standing state.

At time point t2, controller 52 determines that the angular velocity changes from a value smaller than first threshold value T1 to a value equal to or greater than first threshold value T1. In other words, controller 52 determines that the angular velocity reaches first threshold value T1. Therefore, controller 52 causes first electrode 21 to output the electrostimulation, based on the state in which the angular velocity reaches first threshold value T1.

At time point t3, controller 52 determines that the angular velocity changes from the value equal to or greater than first threshold value T1 to a value equal to or smaller than second threshold value T2. In other words, controller 52 determines that the angular velocity reaches second threshold value T2 after reaching first threshold value T1. Therefore, controller 52 causes the outputting from first electrode 21 to be stopped and causes second electrode 22 to output the electrostimulation, based on the state in which the angular velocity reaches second threshold value T2.

At time point t4, controller 52 determines that the angular velocity changes from the value equal to or smaller than second threshold value T2 to a value equal to or greater than first threshold value T1. In other words, controller 52 determines that the angular velocity reaches first threshold value T1 after reaching second threshold value T2. In addition, controller 52 calculates post-stop time period SA1 as a period of elapsed time from time point t3 to time point t4, and compares post-stop time period SA1 with the predetermined post-stop time period set in advance.

In a case where controller 52 determines that post-stop time period SA1 is longer than the predetermined post-stop time period, the controller causes first electrode 21 to output the electrostimulation, based on the state in which the angular velocity reaches first threshold value T1. In comparison, in a case where controller 52 determines that post-stop time period SA1 is shorter than the predetermined post-stop time period, the controller maintains the state in which first electrode 21 stops outputting the electrostimulation. Therefore, at time point t4, controller 52 determines that post-stop time period SA1 is longer than the predetermined post-stop time period, thereby causing the outputting from second electrode 22 to be stopped and causing first electrode 21 to output the electrostimulation, based on the state in which the angular velocity reaches first threshold value T1.

At time point t5, controller 52 determines that the angular velocity reaches second threshold value T2 after reaching first threshold value T1. In addition, controller 52 calculates post-stop time period SA2 as a period of elapsed time from time point t4 to time point t5, and compares post-stop time period SA2 with the predetermined post-stop time period set in advance.

In a case where controller 52 determines that post-stop time period SA2 is longer than the predetermined post-stop time period, the controller causes second electrode 22 to output the electrostimulation, based on the state in which the angular velocity reaches second threshold value T2. In comparison, in a case where controller 52 determines that post-stop time period SA2 is shorter than the predetermined post-stop time period, the controller maintains the state in which second electrode 22 stops outputting the electrostimulation. Therefore, controller 52 determines that post-stop time period SA2 is shorter than the predetermined post-stop time period, thereby causing the outputting from first electrode 21 to be stopped and maintaining the state in which second electrode 22 stops outputting the electrostimulation, based on the state in which the angular velocity reaches second threshold value T2.

At time point t6, controller 52 determines that the angular velocity reaches first threshold value T1 after reaching second threshold value T2. In addition, controller 52 calculates post-stop time period SA1 in the same manner as in the process performed at time point t4, and compares post-stop time period SA1 with the predetermined post-stop time period. Controller 52 determines that post-stop time period SA1 is shorter than the predetermined post-stop time period, thereby maintaining the state in which second electrode 22 stops outputting the electrostimulation and also maintaining the state in which first electrode 21 stops outputting the electrostimulation, based on the state in which the angular velocity reaches first threshold value T1.

At time point t7, controller 52 determines that the angular velocity reaches second threshold value T2 after reaching first threshold value T1. In addition, controller 52 calculates post-stop time period SA2 in the same manner as in the process performed at time point t5, and compares post-stop time period SA2 with the predetermined post-stop time period. Controller 52 determines that post-stop time period SA2 is longer than the predetermined post-stop time period, thereby maintaining the state in which first electrode 21 stops outputting the electrostimulation and causing second electrode 22 to output the electrostimulation, based on the state in which the angular velocity reaches second threshold value T2.

At time point t8, controller 52 determines that the period of duration time (duration), during which a state in which the angular velocity is within a predetermined range is maintained, reaches determined time period PA. Controller 52 causes the outputting from second electrode 22 to be stopped, based on the state in which the duration reaches determined time period PA. Controller 52 calculates the duration whenever the angular velocity changes to the value equal to or smaller than first threshold value T1 or to the value equal to or greater than second threshold value T2, and determines a relationship between the duration and determined time period PA, as needed.

At time point t9, controller 52 determines that the angular velocity reaches first threshold value T1 after reaching second threshold value T2. In addition, controller 52 calculates post-stop time period SA1 in the same manner as in the process performed at time point t4, and compares post-stop time period SA1 with the predetermined post-stop time period. Controller 52 determines that post-stop time period SA1 is longer than the predetermined post-stop time period, thereby maintaining the state in which the outputting from the second electrode is stopped and causing first electrode 21 to output the electrostimulation, based on the state in which the angular velocity reaches first threshold value T1.

In this manner, controller 52 performs the first control, based on the relationship between the angular velocity and each of threshold values T1 and T2, the relationship between post-stop time periods SA1 and SA2 and the predetermined post-stop time period, and the relationship between the duration and determined time period PA. In a case of continuing the bending and extension movements after time point t9, controller 52 repeatedly performs the same processes as the processes performed at time points t4 to t9.

Effects of electrostimulator 1 will be described with reference to FIGS. 1 and 2.

The user using electrostimulator 1 puts supporter 10 for the right leg on the right thigh and puts supporter 10 for the left leg on the left thigh. Here, each of supporters 10 is put on the thigh such that first electrode 21 is disposed at a position facing quadriceps femoris MF and second electrode 22 is disposed at a position facing biceps femoris MT. Then, the user attaches controller 40 to clothes or the like.

Before starting training, the user operates operator 41 so as to switch the power of electrostimulator 1 from OFF to ON. The power of electrostimulator 1 is set to ON, and thereby each of angular velocity sensor 30 starts outputting, to controller 52, the signal, in which an angular velocity of a thigh is reflected. Then, the user starts, for example, the bending and extension movements from a standing state.

Controller 52 performs the first control, based on the relationship between the angular velocity acquired from angular velocity sensor 30 and each or threshold values T1 and T2. Therefore, when the knee joint of the user is bent, the electrostimulation is output from first electrode 21 to quadriceps femoris MF as the antagonist muscle. In addition, when the user extends the knee joint, the electrostimulation is output from second electrode 22 to biceps femoris MT as the antagonist muscle. Therefore, training effects of the bending and extension movements are enhanced.

According to control device 50 of Exemplary Embodiment 1, the following effects are further achieved.

(1) According to control device 50 of electrostimulator 1, the following effects are achieved, compared to another electrostimulator which controls the outputting and the stopping of the electrostimulation applied to a thigh, based on a relationship between an angular velocity and one threshold value.

Motion of a user may not be stable during training For example, in a case where the user makes bending and extension movements, there is a difference between motions of the body in ideal bending and extension movements and actual motions of the body due to swaying of the upper body. In such a state in which the motion of the user is not stable in a case of using the other electrostimulator during training, there is a concern that a state in which the angular velocity exceeds a threshold value and the angular velocity becomes smaller than the threshold value will be repeated in a short cycle. In this case, the outputting and the stopping of the electrostimulation applied to the thigh are repeated in a short cycle, and thus, the user is likely to be uncomfortable.

According to control device 50, the electrostimulation control is performed to control the electrostimulation output from electrodes 21 and 22, based on the relationship between the angular velocity and first threshold value T1 and second threshold value T2. Therefore, although the angular velocity changes due to the unstable motion of the user and, for example, the angular velocity exceeds first threshold value T1, the electrostimulation is not output from second electrode 22 when the angular velocity does not reach second threshold value T2. The same is true of first electrode 21. Therefore, there is less concern that the outputting and the stopping of the electrostimulation will be repeated in the short cycle and the user is unlikely to be uncomfortable.

(2) According to control device 50, first threshold value T1 or second threshold value T2 is used not only for outputting the electrostimulation from electrodes 21 and 22, but also for stopping the outputting from electrodes 21 and 22. Therefore, the amount of information required to be stored in the control device 50 in advance is decreased.

(3) The bending and extension movements include a first period during which the thigh moves from an initial position to a folded position, and a second period during which the thigh moves from the folded position to the initial position. A typical example of unstable motion of a user is a motion in which a speed of the movement of the thigh is changed within the first period or within the second period. According to control device 50, the sign of first threshold value T1 is opposite to the sign of second threshold value T2. Therefore, there is still less concern that the outputting and the stopping of the electrostimulation will be repeated in a short cycle, even though the angular velocity changes due to the unstable motion of the user.

(4) In a case where the motion of the user is stopped, the state in which the angular velocity is within the predetermined range including the angular velocity of 0 is maintained. Based on this state, control device 50 performs output-stop control of stopping electrodes 21 and 22 from outputting the electrostimulation, based on the state in which the period of duration time (duration), during which the angular velocity is within the predetermined range including the angular velocity of 0, reaches determined time period PA set in advance. Therefore, the electrostimulation is not output from electrodes 21 and 22 in the case where the motion of the user is stopped. Hence, the user is unlikely to be uncomfortable.

(5) Since, in the case of the unstable motion of the user, the thigh vibrates in a short cycle, for example, post-stop time periods SA1 and SA2 become shorter. Based on this state, control device 50 performs the stop-maintaining control of maintaining the state in which the outputting from electrodes 21 and 22 is stopped in the case where post-stop time periods SA1 and SA2 are shorter than the predetermined post-stop time period set in advance. Therefore, the outputting and the stopping of the electrostimulation are unlikely to be repeated in the short cycle, even though the angular velocity changes in the short cycle due to the unstable motion of the user.

Exemplary Embodiment 2

Hereinafter, differences between control device 50 of electrostimulator 1 of Exemplary Embodiment 2 and control device 50 of electrostimulator 1 of Exemplary Embodiment 1 will be described, but control device 50 of electrostimulator 1 of Exemplary Embodiment 2 has virtually the same configuration as control device 50 of electrostimulator 1 of Exemplary Embodiment 1 except for the differences. In the following description of control device 50 of electrostimulator 1 of Exemplary Embodiment 2, the same reference signs are assigned to common configurations to control device 50 of electrostimulator 1 of Exemplary Embodiment 1, and a part of or entire description of the common configurations will be omitted.

In a case where the outputting from first electrode 21 is stopped, controller 52 calculates, by using the timer, post-output time period EA1 as a period of time which elapses after the latest electrostimulation starts to be output from first electrode 21, based on the state in which the angular velocity reaches first threshold value T1 after reaching second threshold value T2. In other words, post-output time period EA1 means a period of time from the outputting of the electrostimulation from first electrode 21 to the following output of the electrostimulation from first electrode 21.

In addition, in a case where the outputting from second electrode 22 is stopped, controller 52 calculates, by using the timer, post-output time period EA2 as a period of time which elapses after the latest electrostimulation starts to be output from second electrode 22, based on the state in which the angular velocity reaches second threshold value T2 after reaching first threshold value T1. In other words, post-output time period EA2 means a period of time from the outputting of the electrostimulation from second electrode 22 to the following output of the electrostimulation from second electrode 22.

In a case where the calculated post-output time periods EA1 and EA2 are shorter than a predetermined post-output time period, controller 52 performs another type of stop-maintaining control of maintaining the state in which the outputting from electrodes 21 and 22 is stopped. The predetermined post-output time period is stored in storage 53. Controller 52 performs second control including, for example, the electrostimulation control, the other type of stop-maintaining control, and the output-stop control, and controls the electrostimulation which is output from each of electrodes 21 and 22.

Figure 4A:
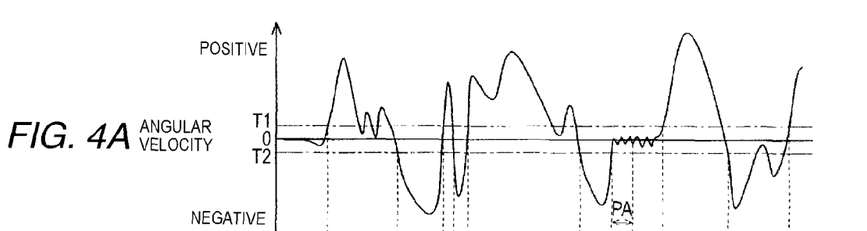
FIGS. 4A to 4C are time charts showing an example of second control.
Figure 4B:
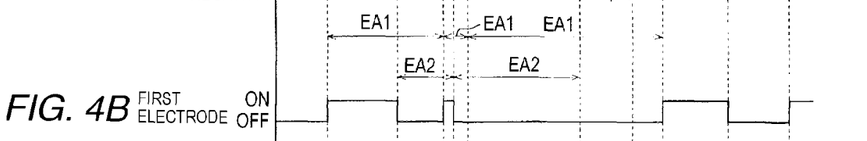
Figure 4C:
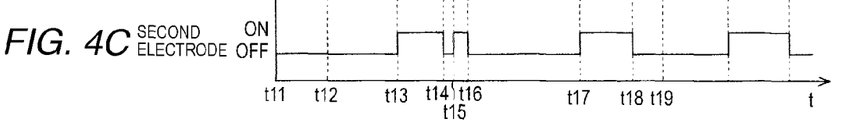

FIGS. 4A to 4C illustrate an example of a relationship between the angular velocity related to the training and the outputting states from electrodes 21 and 22 when the second control is performed. A temporal change of the angular velocity is shown in FIG. 4A, the outputting state from first electrode 21 is shown in FIG. 4B, and the outputting state from second electrode 22 is shown in FIG. 4C. In addition, since virtually the same detection results are obtained from respective angular velocity sensors 30 during the bending and extension movements, a relationship between the angular velocity acquired from one angular velocity sensor 30 and electrodes 21 and 22 corresponding to one angular velocity sensor 30 is described.

At time point t11, a user using electrostimulator 1 operates operator 41 so as to switch the power of electrostimulator 1 from OFF to ON. The power of electrostimulator 1 is set to ON, and thereby each of angular velocity sensors 30 starts outputting, to controller 52, the signal, in which an angular velocity of a thigh is reflected. Then, the user starts, for example, training by cyclic bending and extension movements from a standing state.

At time point t12, controller 52 performs virtually the same process performed at time point t2 illustrated in FIGS. 3A to 3C. At time point t13, controller 52 performs virtually the same process performed at time point t3 illustrated in FIGS. 3A to 3C.

At time point t14, controller 52 determines that the angular velocity reaches first threshold value T1 after reaching second threshold value T2. In addition, controller 52 calculates post-output time period EA1 as a period of elapsed time from time point t12 to time point t14, and compares post-output time period EA1 with the predetermined post-output time period set in advance.

In a case where controller 52 determines that post-output time period EA1 is longer than the predetermined post-output time period, the controller causes first electrode 21 to output the electrostimulation, based on the state in which the angular velocity reaches first threshold value T1. In comparison, in a case where controller 52 determines that post-output time period EA1 is shorter than the predetermined post-output time period, the controller maintains the state in which first electrode 21 stops outputting the electrostimulation. Therefore, at time point t14, controller 52 determines that post-output time period EA1 is longer than the predetermined post-output time period, thereby causing the outputting from second electrode 22 to be stopped and causing first electrode 21 to output the electrostimulation, based on the state in which the angular velocity reaches first threshold value T1.

At time point t15, controller 52 determines that the angular velocity reaches second threshold value T2 after reaching first threshold value T1. In addition, controller 52 calculates post-output time period EA2 as a period of elapsed time from time point t13 to time point t15, and compares post-output time period EA2 with the predetermined post-output time period set in advance.

In a case where controller 52 determines that post-output time period EA2 is longer than the predetermined post-output time period, the controller causes second electrode 22 to output the electrostimulation, based on the state in which the angular velocity reaches second threshold value T2. In comparison, in a case where controller 52 determines that post-output time period EA2 is shorter than the predetermined post-output time period, the controller maintains the state in which second electrode 22 stops outputting the electrostimulation. Therefore, at time point t15, controller 52 determines that post-output time period EA2 is longer than the predetermined post-output time period, thereby causing the outputting from first electrode 21 to be stopped and causing second electrode 22 to output the electrostimulation, based on the state in which the angular velocity reaches second threshold value T2.

At time point t16, controller 52 determines that the angular velocity reaches first threshold value T1 after reaching second threshold value T2. In addition, controller 52 calculates post-output time period EA1 in the same manner as in the process performed at time point t14, and compares post-output time period EA1 with the predetermined post-output time period. Controller 52 determines that post-output time period EA1 is shorter than the predetermined post-output time period, thereby causing second electrode 22 to output the electrostimulation and also maintaining the state in which first electrode 21 stops outputting the electrostimulation, based on the state in which the angular velocity reaches first threshold value T1.

At time point t17, controller 52 determines that the angular velocity reaches second threshold value T2 after reaching first threshold value T1. In addition, controller 52 calculates post-output time period EA2 in the same manner as in the process performed at time point t15, and compares post-output time period EA2 with the predetermined post-output time period. Controller 52 determines that post-output time period EA2 is longer than the predetermined post-output time period, thereby maintaining the state in which first electrode 21 stops outputting the electrostimulation and causing second electrode 22 to output the electrostimulation, based on the state in which the angular velocity reaches second threshold value T2.

At time point t18, controller 52 performs virtually the same process performed at time point t8 illustrated in FIGS. 3A to 3C. At time point t19, controller 52 determines that the angular velocity reaches first threshold value T1 after reaching second threshold value T2. In addition, controller 52 calculates post-output time period EA1 in the same manner as in the process performed at time point t14, and compares post-output time period EA1 with the predetermined post-output time period. Controller 52 determines that post-output time period EA1 is longer than the predetermined post-output time period, thereby maintaining the state in which second electrode stops outputting the electrostimulation and causing first electrode 21 to output the electrostimulation, based on the state in which the angular velocity reaches first threshold value T1.

In this manner, controller 52 performs the second control, based on the relationship between the angular velocity and each of threshold values T1 and T2, the relationship between post-output time periods EA1 and EA2 and the predetermined post-output time period, and the relationship between the duration and determined time period PA. In a case of continuing the bending and extension movements after time point t19, controller 52 repeatedly performs the same processes as the processes performed at time points t14 to t19.

According to control device 50 of Exemplary Embodiment 2, in addition to the effects of (1) to (4) achieved by Exemplary Embodiment 1, the following effect is further achieved.

(6) Since, in the case of the unstable motion of the user, the thigh vibrates in a short cycle, for example, post-output time periods EA1 and EA2 become shorter. Based on this state, control device 50 performs another type of stop-maintaining control of maintaining the state in which the outputting from electrodes 21 and 22 is stopped in the case where post-output time periods EA1 and EA2 are shorter than the predetermined post-output time period set in advance. Therefore, the outputting and the stopping of the electrostimulation are unlikely to be repeated in the short cycle, even though the angular velocity changes in the short cycle due to the unstable motion of the user.

Exemplary Embodiment 3

Hereinafter, differences between control device 50 of electrostimulator 1 of Exemplary Embodiment 3 and control device 50 of electrostimulator 1 of Exemplary Embodiment 1 will be described, but control device 50 of electrostimulator 1 of Exemplary Embodiment 3 has virtually the same configuration as control device 50 of electrostimulator 1 of Exemplary Embodiment 1 except for the differences. In the following description of control device 50 of electrostimulator 1 of Exemplary Embodiment 3, the same reference signs are assigned to common configurations to control device 50 of electrostimulator 1 of Exemplary Embodiment 1, and a part of or entire description of the common configurations will be omitted.

Controller 52 calculates, by using the timer, a period of duration time (duration) during which the angular velocity is within a predetermined range including the angular velocity of 0. An example of the predetermined range is a range which is defined by upper limit threshold value TU greater than first threshold value T1 and lower limit threshold value TD smaller than second threshold value T2. Controller 52 performs the other type of output-stop control such that the outputting from electrodes 21 and 22 is stopped, based on a state in which the duration reaches determined time period PB as a predetermined period of time set in advance. Determined time period PB is stored in storage 53. Controller 52 performs third control including, for example, the electrostimulation control and the other type of output-stop control, and controls the electrostimulation which is output from each of electrodes 21 and 22.

Figure 5A:
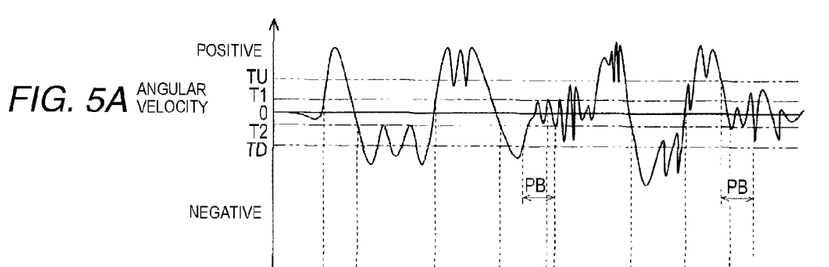
FIGS. 5A to 5C are time charts showing an example of third control.
Figure 5B:
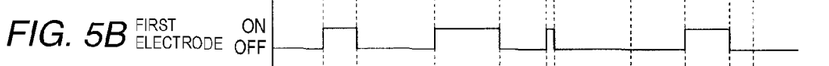
Figure 5C:
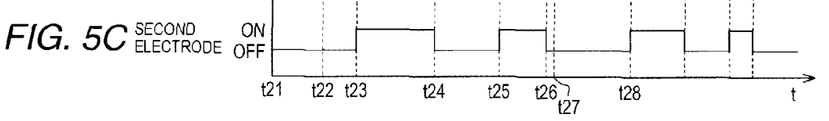

FIG. 5A to 5C illustrate an example of a relationship between the angular velocity related to the training and the outputting states from electrodes 21 and 22 when the third control is performed. A temporal change of the angular velocity is shown in FIG. 5A, the outputting state from first electrode 21 is shown in FIG. 5B, and the outputting state from second electrode 22 is shown in FIG. 5C. In addition, since virtually the same detection results are obtained from respective angular velocity sensors 30 during the bending and extension movements, a relationship between the angular velocity acquired from one angular velocity sensor 30 and electrodes 21 and 22 corresponding to one angular velocity sensor 30 is described.

At time point t21, the user using electrostimulator 1 operates operator 41 so as to switch the power of electrostimulator 1 from OFF to ON. The power of electrostimulator 1 is set to ON, and thereby each of angular velocity sensors 30 starts outputting, to controller 52, the signal, in which the angular velocity of the thigh is reflected. Then, the user starts, for example, training by cyclic bending and extension movements from the standing state.

At time point t22, controller 52 determines that the angular velocity reaches first threshold value T1. Therefore, controller 52 causes first electrode 21 to output the electrostimulation. At time point t23, controller 52 determines that the angular velocity reaches second threshold value T2 after reaching first threshold value T1. Therefore, controller 52 causes the outputting from first electrode 21 to be stopped and causes second electrode 22 to output the electrostimulation, based on the state in which the angular velocity reaches second threshold value T2.

At time point t24, controller 52 determines that the angular velocity reaches first threshold value T1 after reaching second threshold value T2. Therefore, controller 52 causes the outputting from second electrode 22 to be stopped and causes first electrode 21 to output the electrostimulation, based on the state in which the angular velocity reaches first threshold value T1.

At time point t25, controller 52 performs virtually the same process performed at time point t23. At time point t26, controller 52 performs virtually the same process performed at time point t24.

At time point t27, controller 52 determines that the period of duration time (duration), during which a state in which the angular velocity is within a predetermined range is maintained, reaches determined time period PB. Controller 52 causes the outputting from first electrode 21 to be stopped, based on the state in which the duration reaches determined time period PB. Controller 52 maintains a state in which the outputting from electrodes 21 and 22 is stopped until the angular velocity changes to the value equal to or greater than upper limit threshold value TU or to the value equal to or smaller than lower limit threshold value TD. Controller 52 calculates the duration whenever the angular velocity changes to the value equal to or smaller than upper limit threshold value TU or to the value equal to or greater than lower limit threshold value TD, and determines a relationship between the duration and determined time period PB, as needed.

At time point t28, controller 52 determines that the angular velocity changes to the value equal to or greater than upper limit threshold value TU, and then, the angular velocity reaches second threshold value T2 after reaching first threshold value T1. Therefore, controller 52 maintains the state in which first electrode 21 stops outputting the electrostimulation and causes second electrode 22 to output the electrostimulation, based on the state in which the angular velocity reaches second threshold value T2.

In this manner, controller 52 performs the third control, based on the relationship between the angular velocity and each of threshold values T1 and T2, and the relationship between the duration and determined time period PB. In a case of continuing the bending and extension movements after time point t28, controller 52 repeatedly performs the same processes as the processes performed at time points t23 to t28. In addition, according to control device 50 of Exemplary Embodiment 3, virtually the same effects as the effects of (1) to (4) achieved by Exemplary Embodiment 1 are achieved.

Exemplary Embodiment 4

Hereinafter, differences between control device 50 of electrostimulator 1 of Exemplary Embodiment 4 and control device 50 of electrostimulator 1 of Exemplary Embodiment 1 will be described, but control device 50 of electrostimulator 1 of Exemplary Embodiment 4 has virtually the same configuration as control device 50 of electrostimulator 1 of Exemplary Embodiment 1 except for the differences. In the following description of control device 50 of electrostimulator 1 of Exemplary Embodiment 4, the same reference signs are assigned to common configurations to control device 50 of electrostimulator 1 of Exemplary Embodiment 1, and a part of or entire description of the common configurations will be omitted.

Storage 53 stores first output threshold value TE1 which is compared with the angular velocity for controlling the outputting state from first electrode 21, and first stop threshold value TS1 which is compared with the angular velocity for controlling the outputting state from first electrode 21 and which is smaller than first output threshold value TE1. The sign of first output threshold value TE1 is opposite to the sign of first stop threshold value TS1. In other words, first output threshold value TE1 exists in a positive region and first stop threshold value TS1 exists in a negative region.

Controller 52 reads respective threshold values TE1 and TS1 from storage 53 and causes first electrode 21 to output the electrostimulation, based on the state in which the angular velocity reaches first output threshold value TE1 after reaching first stop threshold value TS1. Therefore, the electrostimulation is applied to quadriceps femoris MF as the antagonist muscle. Then, in the case where the electrostimulation is output from first electrode 21, controller 52 causes the outputting from first electrode 21 to be stopped, based on the state in which the angular velocity reaches first stop threshold value TS1.

Storage 53 further stores second output threshold value TE2 which is compared with the angular velocity for controlling the outputting state from second electrode 22, and second stop threshold value TS2 which is compared with the angular velocity for controlling the outputting state from second electrodes 22 and which is greater than second output threshold value TE2. The sign of second output threshold value TE2 is opposite to the sign of second stop threshold value TS2. In other words, second output threshold value TE2 exists in the negative region and second stop threshold value TS2 exists in the positive region. In addition, first output threshold value TE1 is greater, for example, than second stop threshold value TS2, and second output threshold value TE2 is smaller, for example, than first stop threshold value TS1.

Controller 52 reads respective threshold values TE2 and TS2 from storage 53 and causes second electrode 22 to output the electrostimulation, based on the state in which the angular velocity reaches second output threshold value TE2 after reaching second stop threshold value TS2. Therefore, the electrostimulation is applied to biceps femoris MT as the antagonist muscle. Then, in the case where the electrostimulation is output from second electrode 22, controller 52 causes the outputting from second electrode 22 to be stopped, based on the state in which the angular velocity reaches second stop threshold value TS2. In this manner, controller 52 performs fourth control including another type of electrostimulation control of controlling the electrostimulation output from electrodes 21 and 22, based on the relationship between the angular velocity and each of threshold values TE1 and TS1, and the relationship between the angular velocity and each of threshold values TE2 and TS2.

Figure 6A:
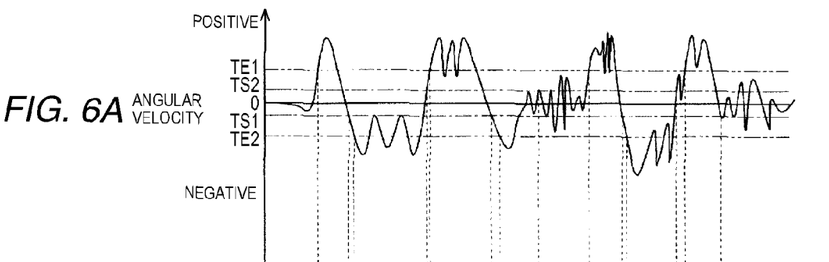
FIGS. 6A to 6C are time charts showing an example of fourth control.
Figure 6B:
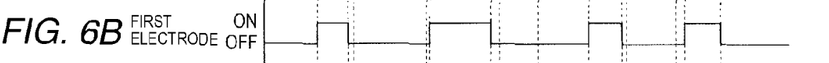
Figure 6C:
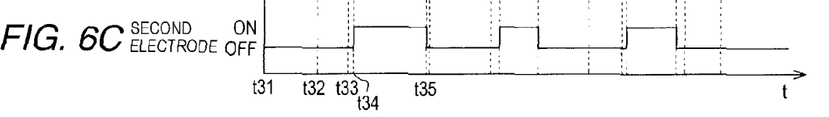

FIGS. 6A to 6C illustrate an example of a relationship between the angular velocity related to the training and the outputting states from electrodes 21 and 22 when the fourth control is performed. A temporal change of the angular velocity is shown in FIG. 6A, the outputting state from first electrode 21 is shown in FIG. 6B, and the outputting state from second electrode 22 is shown in FIG. 6C. In addition, since virtually the same detection results are obtained from respective angular velocity sensors 30 during the bending and extension movements, a relationship between the angular velocity acquired from one angular velocity sensor 30 and electrodes 21 and 22 corresponding to one angular velocity sensor 30 is described.

At time point t31, the user using electrostimulator 1 operates operator 41 so as to switch the power of electrostimulator 1 from OFF to ON. The power of electrostimulator 1 is set to ON, and thereby each of angular velocity sensors 30 starts outputting, to controller 52, the signal, in which the angular velocity of the thigh is reflected. Then, the user starts, for example, training by cyclic bending and extension movements from the standing state.

At time point t32, controller 52 determines that the angular velocity reaches first output threshold value TE1. Therefore, controller 52 causes first electrode 21 to output the electrostimulation. At time point t33, controller 52 determines that the angular velocity reaches first stop threshold value TS1. Therefore, controller 52 causes the outputting from first electrode 21 to be stopped.

At time point t34, controller 52 determines that the angular velocity reaches second output threshold value TE2 after reaching second stop threshold value TS2. Therefore, controller 52 causes second electrode 22 to output the electrostimulation. At time point t35, controller 52 determines that the angular velocity reaches second stop threshold value TS2. Therefore, controller 52 causes the outputting from second electrode 22 to be stopped.

In this manner, controller 52 performs the fourth control, based on the relationship between the angular velocity and each of threshold values TE1 and TS1, and the relationship between the angular velocity and each of threshold values TE2 and TS2. In a case of continuing the bending and extension movements after time point t35, controller 52 repeatedly performs the same processes as the processes performed at time points t32 to t35. In addition, according to control device 50 of Exemplary Embodiment 4, virtually the same effects as the effects of (1) to (3) achieved by Exemplary Embodiment 1 are achieved.

Exemplary Embodiment 5

Hereinafter, differences between control device 50 of electrostimulator 1 of Exemplary Embodiment 5 and control device 50 of electrostimulator 1 of Exemplary Embodiment 4 will be described, but control device 50 of electrostimulator 1 of Exemplary Embodiment 5 has virtually the same configuration as control device 50 of electrostimulator 1 of Exemplary Embodiment 4 except for the differences. In the following description of control device 50 of electrostimulator 1 of Exemplary Embodiment 5, the same reference signs are assigned to common configurations to control device 50 of electrostimulator 1 of Exemplary Embodiment 4, and a part of or entire description of the common configurations will be omitted.

Storage 53 stores first output threshold value TE1 which is compared with the angular velocity for controlling the outputting state from first electrode 21, and first stop threshold value TS1 which is compared with the angular velocity for controlling the outputting state from first electrode 21 and which is smaller than first output threshold value TE1. The sign of first output threshold value TE1 is the same as the sign of first stop threshold value TS1 and, for example, both values exist in the positive region.

Storage 53 further stores second output threshold value TE2 which is compared with the angular velocity for controlling the outputting state from second electrode 22, and second stop threshold value TS2 which is compared with the angular velocity for controlling the outputting state from second electrodes 22 and which is greater than second output threshold value TE2. The sign of second output threshold value TE2 is the same as the sign of second stop threshold value TS2, and both values exist in the negative region. In this manner, controller 52 performs fifth control including still another type of electrostimulation control of controlling the electrostimulation output from electrodes 21 and 22, based on the relationship between the angular velocity and each of threshold values TE1 and TS1, and the relationship between the angular velocity and each of threshold values TE2 and TS2.

Figure 7A:
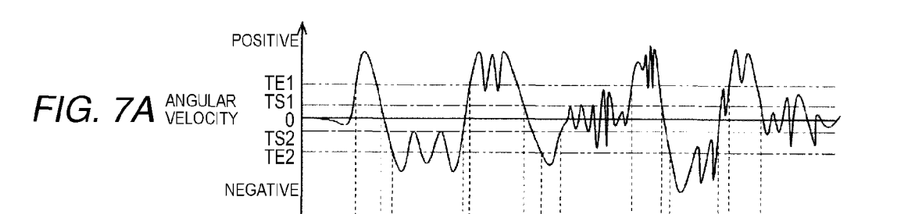
FIGS. 7A to 7C are time charts showing an example of fifth control.
Figure 7B:
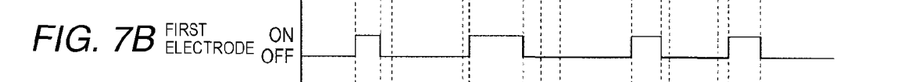
Figure 7C:
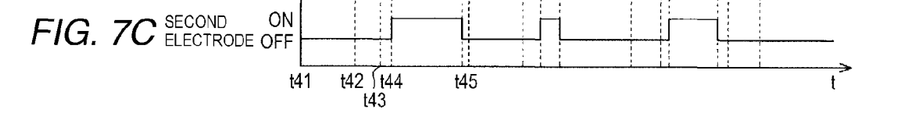

FIGS. 7A to 7C illustrate an example of a relationship between the angular velocity related to the training and the outputting states from electrodes 21 and 22 when the fifth control is performed. A temporal change of the angular velocity is shown in FIG. 7A, the outputting state from first electrode 21 is shown in FIG. 7B, and the outputting state from second electrode 22 is shown in FIG. 7C. In addition, since virtually the same detection results are obtained from respective angular velocity sensors 30 during the bending and extension movements, a relationship between the angular velocity acquired from one angular velocity sensor 30 and electrodes 21 and 22 corresponding to one angular velocity sensor 30 is described.

At time point t41, the user using electrostimulator 1 operates operator 41 so as to switch the power of electrostimulator 1 from OFF to ON. The power of electrostimulator 1 is set to ON, and thereby each of angular velocity sensors 30 starts outputting, to controller 52, the signal, in which the angular velocity of the thigh is reflected. Then, the user starts, for example, training by cyclic bending and extension movements from the standing state.

At time point t42, controller 52 determines that the angular velocity reaches first output threshold value TE1. Therefore, controller 52 causes first electrode 21 to output the electrostimulation. At time point t43, controller 52 determines that the angular velocity reaches first stop threshold value TS1. Therefore, controller 52 causes the outputting from first electrode 21 to be stopped.

At time point t44, controller 52 determines that the angular velocity reaches second output threshold value TE2 after reaching second stop threshold value TS2. Therefore, controller 52 causes second electrode 22 to output the electrostimulation. At time point t45, controller 52 determines that the angular velocity reaches second stop threshold value TS2. Therefore, controller 52 causes the outputting from second electrode 22 to be stopped.

In this manner, controller 52 performs the fifth control, based on the relationship between the angular velocity and each of threshold values TE1 and TS1, and the relationship between the angular velocity and each of threshold values TE2 and TS2. In a case of continuing the bending and extension movements after time point t45, controller 52 repeatedly performs the same processes as the processes performed at time points t42 to t45. In addition, according to control device 50 of Exemplary Embodiment 5, virtually the same effects as the effects achieved by Exemplary Embodiment 4 are achieved.

Exemplary Embodiment 6

Hereinafter, differences between control device 50 of electrostimulator 1 of Exemplary Embodiment 6 and control device 50 of electrostimulator 1 of Exemplary Embodiment 1 will be described, but control device 50 of electrostimulator 1 of Exemplary Embodiment 6 has virtually the same configuration as control device 50 of electrostimulator 1 of Exemplary Embodiment 1 except for the differences. In the following description of control device 50 of electrostimulator 1 of Exemplary Embodiment 6, the same reference signs are assigned to common configurations to control device 50 of electrostimulator 1 of Exemplary Embodiment 1, and a part of or entire description of the common configurations will be omitted.

Controller 52 performs first electrostimulation control as the electrostimulation control of controlling the electrostimulation output from electrodes 21 and 22, based on the relationship between the angular velocity and each of threshold values T1 and T2. The angular velocity may significantly change due to a speed of the training movement of the user.

Storage 53 stores, in addition to first threshold value T1 and second threshold value T2, third threshold value T3 which is compared with the angular velocity for controlling the outputting state from each of electrodes 21 and 22, and fourth threshold value T4 which is compared with the angular velocity for controlling the outputting state from each of electrodes 21 and 22, and which is smaller than third threshold value T3. The sign of third threshold value T3 is opposite to the sign of fourth threshold value T4. Third output threshold value T3 is greater, for example, than first threshold value T1, and fourth threshold value T4 is smaller, for example, than second threshold value T2. Controller 52 reads respective threshold values T3 and T4 from storage 53 and performs second electrostimulation control of controlling the electrostimulation output from electrodes 21 and 22, based on the relationship between the angular velocity and each of threshold values T3 and T4. The second electrostimulation control is performed instead of the first electrostimulation control, based on a state in which the angular velocity reaches third threshold value T3 or fourth threshold value T4.

In a case where the first electrostimulation control is performed, controller 52 performs switching from the first electrostimulation control to the second electrostimulation control, based on a state in which the angular velocity reaches first threshold value T1 and further reaches third threshold value T3 after reaching second threshold value T2. Then, in the case where the electrostimulation is output from first electrode 21, controller 52 causes the outputting from first electrode 21 to be stopped, based on a state in which the angular velocity reaches fourth threshold value T4. In addition, controller 52 causes first electrode 21 to output the electrostimulation, based on a state in which the angular velocity reaches third threshold value T3 after reaching fourth threshold value T4.

In comparison, in the case where the first electrostimulation control is performed, controller 52 performs switching from the first electrostimulation control to the second electrostimulation control, based on a state in which the angular velocity reaches second threshold value T2 and further reaches fourth threshold value T4 after reaching first threshold value T1. Then, in the case where the electrostimulation is output from second electrode 22, controller 52 causes the outputting from second electrode 22 to be stopped, based on a state in which the angular velocity reaches third threshold value T3. In addition, controller 52 causes second electrode 22 to output the electrostimulation, based on a state in which the angular velocity reaches fourth threshold value T4 after reaching third threshold value T3. Further, in a case where the second electrostimulation control is performed, controller 52 performs switching from the second electrostimulation control to the first electrostimulation control, in a case where a state in which the angular velocity is within a predetermined range defined by third threshold value T3 and fourth threshold value T4 is maintained for a predetermined period of time Controller 52 performs sixth control including the first electrostimulation control and the second electrostimulation control, and controls the electrostimulation output from each of electrodes 21 and 22.

Figure 8A:
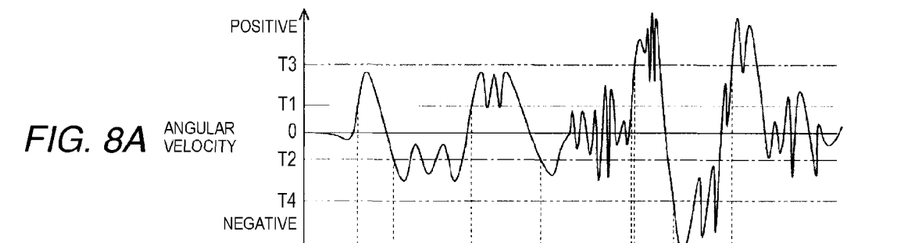
FIGS. 8A to 8C are time charts showing an example of sixth control.
Figure 8B:
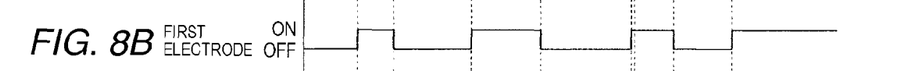
Figure 8C:
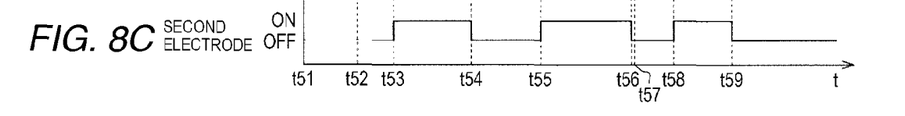

FIG. 8 illustrates an example of a relationship between the angular velocity related to the training and the outputting states from electrodes 21 and 22 when the sixth control is performed. A temporal change of the angular velocity is shown in FIG. 8A, the outputting state from first electrode 21 is shown in FIG. 8B, and the outputting state from second electrode 22 is shown in FIG. 8C. In addition, since virtually the same detection results are obtained from angular velocity sensors 30 during the bending and extension movements, a relationship between the angular velocity acquired from one angular velocity sensor 30 and electrodes 21 and 22 corresponding to one angular velocity sensor 30 is described.

At time point t51, the user using electrostimulator 1 operates operator 41 so as to switch the power of electrostimulator 1 from OFF to ON. The power of electrostimulator 1 is set to ON, and thereby each of angular velocity sensors 30 starts outputting, to controller 52, the signal, in which the angular velocity of the thigh is reflected. Then, the user starts, for example, training by cyclic bending and extension movements from the standing state.

At time point t52, controller 52 determines that the angular velocity reaches first threshold value T1. Therefore, controller 52 causes first electrode 21 to output the electrostimulation. At time point t53, controller 52 determines that the angular velocity reaches second threshold value T2 after reaching first threshold value T1. Therefore, controller 52 causes the outputting from first electrode 21 to be stopped and causes second electrode 22 to output the electrostimulation, based on the state in which the angular velocity reaches second threshold value T2.

At time point t54, controller 52 determines that the angular velocity reaches first threshold value T1 after reaching second threshold value T2. Therefore, controller 52 causes the outputting from second electrode 22 to be stopped and causes first electrode 21 to output the electrostimulation, based on the state in which the angular velocity reaches the first threshold value.

At time point t55, controller 52 performs virtually the same process performed at time point t53. At time point t56, controller 52 performs virtually the same process performed at time point t54.

At time point t57, controller 52 determines that the angular velocity reaches third threshold value T3. Therefore, controller 52 performs switching from the first electrostimulation control to the second electrostimulation control. After time point t57, controller 52 performs switching from the second electrostimulation control to the first electrostimulation control, in a case where it is determined that the state in which the angular velocity is within the predetermined range defined by third threshold value T3 and fourth threshold value T4 is maintained for the predetermined period of time.

At time point t58, controller 52 determines that the angular velocity reaches fourth threshold value T4 after reaching third threshold value T3. Therefore, controller 52 causes the outputting from first electrode 21 to be stopped and causes second electrode 22 to output the electrostimulation, based on the state in which the angular velocity reaches fourth threshold value T4.

At time point t59, controller 52 determines that the angular velocity reaches third threshold value T3 after reaching fourth threshold value T4. Therefore, controller 52 causes the outputting from second electrode 22 to be stopped and causes first electrode 21 to output the electrostimulation, based on the state in which the angular velocity reaches third threshold value T3.

In this manner, controller 52 performs the sixth control, based on the relationship between the angular velocity and each of threshold values T1 and T2, and the relationship between the angular velocity and each of threshold values T3 and T4. In a case of continuing the bending and extension movements after time point t59, controller 52 repeatedly performs the same processes as the processes performed at time points t53 to t59.

According to control device 50 of Exemplary Embodiment 6, in addition to the effects of (1) to (3) achieved by Exemplary Embodiment 1, the following effect is further achieved.

(7) In a case of a high speed of the training movement, there is a high concern that the outputting and the stopping of the electrostimulation are repeated in the short cycle. Based on this state, in a case where it is assumed that the training movement is made at a high speed, control device 50 is switched to the second electrostimulation control from the first electrostimulation control. Therefore, even in the case of the high speed of the training movement, there is still less concern that the outputting and the stopping of the electrostimulation are repeated in the short cycle, compared to the case of the first electrostimulation control.

Modification Example

The exemplary embodiments are described above as examples of exemplary embodiments of the electrostimulator and the control device of the electrostimulator according to the present disclosure, and the exemplary embodiments thereof are not limited to the exemplary embodiments described above. The electrostimulator and the control device of the electrostimulator according to the present disclosure can be realized, for example, as the following modification examples of the exemplary embodiments described above, and as an exemplary embodiment achieved by combining at least two modification examples which are not incompatible, as well as the exemplary embodiment described above.

Controller 52 of a modification example of Exemplary Embodiment 1 performs another type of first control in which at least one of the stop-maintaining control or the outputting-stop control is omitted from the first control. In a case where the other type of first control in which both the stop-maintaining control and the outputting-stop control are omitted from the first control, the timer may be omitted from controller 52.

In the case where the other type of first control, in which the stop-maintaining control is omitted from the first control, is performed, differences between the other type of first control and the first control will be described below, and virtually the same control as the first control is performed in the other type of first control except for the differences. At time point t5 illustrated in FIGS. 3A to 3C, controller 52 causes the outputting from first electrode 21 to be stopped and causes second electrode 22 to output the electrostimulation, based on the state in which the angular velocity reaches second threshold value T2. At time point t6 illustrated in FIGS. 3A to 3C, controller 52 causes the outputting from second electrode 22 to be stopped and causes first electrode 21 to output the electrostimulation, based on the state in which the angular velocity reaches first threshold value T1. At time point t7 illustrated in FIGS. 3A to 3C, controller 52 causes the outputting from first electrode 21 to be stopped and causes second electrode 22 to output the electrostimulation, based on the state in which the angular velocity reaches second threshold value T2.

In the case where the other type of first control, in which the outputting-stop control is omitted from the first control, is performed, differences between the other type of first control and the first control will be described below, and virtually the same control as the first control is performed in the other type of first control except for the differences. Controller 52 omits the process performed at time point t8 illustrated in FIGS. 3A to 3C. In other words, at time point t8, controller 52 causes second electrode 22 to continuously output the electrostimulation. At time point t9 illustrated in FIGS. 3A to 3C, controller 52 causes the outputting from second electrode to be stopped and causes first electrode 21 to output the electrostimulation, based on the state in which the angular velocity reaches first threshold value T1. Further, in a case where the outputting-stop control is omitted from the second control performed by controller 52 of Exemplary Embodiment 2, the same modification is also achieved.

Controller 52 of another modification example of Exemplary Embodiment 1 performs return control of controlling the electrostimulation output from electrodes 21 and 22, based on the relationship between the angular velocity at the time of determination and each of threshold values T11 and T2, in a case where it is determined that a predetermined period of time elapses after the state in which the outputting from electrodes 21 and 22 is stopped is maintained by the stop-maintaining control.

In other words, controller 52 determines whether or not the predetermined period of time elapses after time point t6 illustrated in FIGS. 3A to 3C. Controller 52 determines that the predetermined period of time elapses after time point t6 in a period from time point t6 to time point t7 illustrated in FIGS. 3A to 3C, thereby causing first electrode 21 to output the electrostimulation, based on the state in which the angular velocity at the time of determination is greater than first threshold value T1. In addition, at time point t7, controller 52 causes the outputting from first electrode 21 to be stopped and causes second electrode 22 to output the electrostimulation, based on the state in which the angular velocity reaches second threshold value T2 after reaching first threshold value T1. In Exemplary Embodiment 2, the same modification is also achieved.

Whether or not the sign of first threshold value T1 is opposite to the sign of second threshold value T2 is an option. According to an example, first threshold value T1 exists in the positive region and second threshold value T2 is virtually a value of 0. According to the modification example thereof, for example, in addition to second threshold value T2, an output threshold value which is compared with the angular velocity for controlling the outputting state from second electrode 22 is stored in storage 53. The output threshold value exists in the negative region.

In other words, controller 52 causes second electrode 22 to output the electrostimulation, based on the state in which the angular velocity reaches the output threshold value after reaching second threshold value T2. Then, in the case where the electrostimulation is output from second electrode 22, controller 52 causes the outputting from second electrode 22 to be stopped, based on the state in which the angular velocity reaches second threshold value T2.

According to another modification example, storage 53 stores the first stop threshold value which is compared with the angular velocity for causing the outputting from first electrode 21 to be stopped, and the second stop threshold value which is compared with the angular velocity for causing the outputting from second electrode 22 to be stopped. For example, the first stop threshold value exists between first threshold value T1 and second threshold value T2. For example, the second stop threshold value exists between the output threshold value and second threshold value T2.

In other words, controller 52 causes first electrode 21 to output the electrostimulation, based on the state in which the angular velocity reaches first threshold value T1 after reaching second threshold value T2. Then, in the case where the electrostimulation is output from first electrode 21, controller 52 causes the outputting from first electrode 21 to be stopped, based on the state in which the angular velocity reaches first threshold value T1. Controller 52 causes second electrode 22 to output the electrostimulation, based on the state in which the angular velocity reaches the output threshold value after reaching second threshold value T2. Then, in the case where the electrostimulation is output from second electrode 22, controller 52 causes the outputting from second electrode 22 to be stopped, based on the state in which the angular velocity reaches second stop threshold value.

In the case where the electrostimulation is output from first electrode 21, controller 52 of still another modification example of Exemplary Embodiment 1 causes first electrode 21 to output the electrostimulation, based on the state in which the angular velocity reaches first threshold value T1. In addition, in the case where the electrostimulation is output from second electrode 22, controller 52 of the modification example causes the outputting from second electrode 22 to be stopped, based on the state in which the angular velocity reaches second threshold value T2.

Controller 52 of still another modification example of Exemplary Embodiment 1 performs the other type of first control including another type of stop-maintaining control of Exemplary Embodiment 2, in addition to the electrostimulation control, the stop-maintaining control, and the outputting-stop control. According to the modification example, the predetermined post-output time period is set to be as short as twice the predetermined post-stop time period.

Storage 53 of still another modification example of Exemplary Embodiment 1 stores the predetermined post-stop time period corresponding to post-stop time period SA1 and the predetermined post-stop time period corresponding to post-stop time period SA2. According to an example, the predetermined post-stop time period corresponding to post-stop time period SA2 is longer than the predetermined post-stop time period corresponding to post-stop time period SA1.

Controller 52 of still another modification example of Exemplary Embodiment 3 performs another type of third control including at least one of the stop-maintaining control or the other type of stop-maintaining control, in addition to the electrostimulation control and the other type of outputting-stop control.

A predetermined range defined by the other type of outputting-stop control performed by controller 52 of Exemplary Embodiment 3 is an option. According to an example, the predetermined range is a range defined by upper limit threshold value TU smaller than first threshold value T1 and lower limit threshold value TD greater than second threshold value T2.

Controller 52 of a modification example of Exemplary Embodiment 4 performs another type of fourth control including another type of electrostimulation control, at least one of the stop-maintaining control or the other type of stop-maintaining control, and further the outputting-stop control or the other type of outputting-stop control.

Controller 52 of a modification example of Exemplary Embodiment 5 performs another type of fifth control including still another type of electrostimulation control, at least one of the stop-maintaining control or the other type of stop-maintaining control, and further the outputting-stop control or the other type of outputting-stop control.

In still another type of electrostimulation control performed by controller 52 of Exemplary Embodiment 5, a relationship between first output threshold value TE1 and first stop threshold value TS1 which are compared with the angular velocity for controlling the outputting state of first electrode 21 is an option. According to an example, first output threshold value TE1 is smaller than first stop threshold value TS1.

In still another type of electrostimulation control performed by controller 52 of Exemplary Embodiment 5, a relationship between second output threshold value TE2 and second stop threshold value TS2 which are compared with the angular velocity for controlling the outputting state of second electrode 22 is an option. According to an example, second output threshold value TE2 is greater than second stop threshold value TS2.

Controller 52 of a modification example of Exemplary Embodiment 6 performs another type of sixth control including at least one of the stop-maintaining control or the other type of stop-maintaining control, and further the outputting-stop control or the other type of outputting-stop control, in addition to the first electrostimulation control and the second electrostimulation control.

Power supply 43 of a modification example supplies, to control device 50, power obtained from a commercial power supply, instead of the primary battery or the secondary battery.

Notifier 42 of a modification example outputs information in voice.

Electrostimulator 1 of a modification example includes a touch panel display having a function of operator 41 and a function of notifier 42, instead of operator 41 and notifier 42.

Electrostimulator 1 of a modification example may also omit notifier 42 from controller 40.

Electrostimulator 1 of a modification example includes an acceleration sensor as another detector, instead of angular velocity sensor 30.

Electrostimulator 1 of a modification example can have a configuration in which angular velocity sensor 30 attached to one supporter 10 is omitted. According to the modification example, the electrostimulation which is output from each of electrodes 21 and 22 is controlled, based on the detection result from one angular velocity sensor 30.

Whether or not controller 52 causes each of electrodes 21 and 22 to output the electrostimulation to the antagonist muscle is an option. According to an example, controller 52 causes each of electrodes 21 and 22 to output the electrostimulation to the agonist muscle. In this case, since biceps femoris MT contracts as the agonist muscle when the knee joint is bent, controller 52 causes second electrode 22 to output the electrostimulation. In addition, since quadriceps femoris MF contracts as the agonist muscle when the knee joint is extended, controller 52 causes first electrode 21 to output the electrostimulation.

Whether or not electrostimulator 1 is used during the bending and extension movements is an option. In a case where electrostimulator 1 is used during arm curl as another example of the reciprocating movement, supporter 10 is put on an arm. In this case, electrodes 21 and 22 are disposed at positions facing biceps femoris and triceps femoris in the state in which supporter 10 is put on the arm.

The electrostimulator and the control device of the electrostimulator can be used during the training of sites of a human body including the bending and extension movements.

What is claimed is:

1. A control device of an electrostimulator, which is used in the electrostimulator including an electrode that outputs electrostimulation to a target site of a human body which repeats reciprocating movements, and a detector that outputs a signal in which a movement of the target site is reflected, the control device comprising:
   a controller that controls electrostimulation which is output from the electrode based on a detected value obtained in response to the signal from the detector; and
   a storage that stores a first threshold value which is compared with the detected value so as to control an outputting state from the electrode, and a second threshold value which is compared with the detected value so as to control the outputting state from the electrode and which is smaller than the first threshold value,
   wherein the controller causes the electrode to output electrostimulation based on a state in which the detected value reaches one threshold value of the first threshold value and the second threshold value, and then, reaches the other threshold value of the first threshold value and the second threshold value in an interval equal to or greater than a predetermined time period.

2. The control device of an electrostimulator of claim 1, wherein, after a case where electrostimulation is output from the electrode, the controller causes the outputting from the electrode to be stopped, based on a state in which the detected value reaches the one threshold value of the first threshold value and the second threshold value.

3. The control device of an electrostimulator of claim 2, wherein the electrode includes a first electrode and a second electrode,
   after a case where electrostimulation is output from the first electrode, the controller causes the outputting from the first electrode to be stopped, based on a state in which the detected value reaches the second threshold value, and
   after a case where electrostimulation is output from the second electrode, the controller causes the outputting from the second electrode to be stopped, based on a state in which the detected value reaches the first threshold value.

4. The control device of an electrostimulator of claim 1, wherein a sign of the first threshold value is opposite to a sign of the second threshold value.

5. The control device of the electrostimulator of claim 2, wherein after the outputting from the electrode is stopped, the controller calculates a post-stop time period as a period of elapsed time beginning when the detected value reaches the one threshold value of the first threshold value and the second threshold value and terminating when the detected value reaches the other threshold value of the first threshold value and second threshold value, and wherein the controller maintains a state in which the outputting from the electrode is stopped when the calculated post-stop time period is shorter than a predetermined post-stop time period.

6. The control device of the electrostimulator of claim 2, wherein the controller calculates a post-output time period as a period of elapsed time between a start of the latest electrostimulation that is output from the electrode and a most immediately previous start time of an electrostimulation output from the electrode, wherein an intervening off time exists between the start time of the latest stimulation output from the electrode and the start time of the most immediately previous start time of the electrostimulation output by the electrode, and wherein the controller maintains a state in which the outputting of the latest electrostimulation from the electrode is stopped when the calculated post-output time period is shorter than a predetermined post-output time period.

7. The control device of an electrostimulator of claim 1, wherein the controller causes the outputting from the electrode to be stopped, based on a state in which a period of time for which the detected value is within a predetermined range including 0 is equal to or longer than a predetermined period of time.

8. An electrostimulator comprising:
an electrode;
a detector; and
the control device of claim 1.

9. The control device of an electrostimulator of claim 1, wherein the electrode includes a first electrode and a second electrode,
the controller causes the first electrode to output electrostimulation based on a state in which the detected value reaches the second threshold value, and then, reaches the first threshold value, and
the controller causes the second electrode to output electrostimulation based on a state in which the detected value reaches the first threshold value, and then, reaches the second threshold value.

10. The control device of an electrostimulator of claim 9, wherein the first electrode is disposed at positions facing first muscle, and
the second electrode is disposed at positions facing second muscle, the second muscle being different from first muscle.

* * * * *